United States Patent
Eddy et al.

[11] Patent Number: 6,131,232
[45] Date of Patent: Oct. 17, 2000

[54] COMPACT APPLICATOR/REMOVAL SYSTEM

[76] Inventors: Colleen Eddy, 303 Linden St, Manchester, N.H. 03104; Karen Norberg, 991 Malaihi Rd., Waiehu, Hi. 96793

[21] Appl. No.: 09/252,749

[22] Filed: Feb. 19, 1999

[51] Int. Cl.$^7$ .................................................. A47K 7/02
[52] U.S. Cl. ............................................. 15/222; 601/137
[58] Field of Search .............................. 15/222; 601/137, 601/138, 143

[56] References Cited

U.S. PATENT DOCUMENTS

| | | |
|---|---|---|
| 2,691,787 | 10/1954 | Rosenwein . |
| 3,124,822 | 3/1964 | Marchese . |
| 5,013,171 | 5/1991 | Almond, II ............................... 15/222 |
| 5,035,523 | 7/1991 | Allinder ................................... 15/222 |
| 5,386,609 | 2/1995 | Xenos ...................................... 15/222 |
| 5,545,456 | 8/1996 | Suida ....................................... 15/222 |
| 5,664,281 | 9/1997 | Pelfrey .................................... 15/222 |
| 5,850,662 | 12/1996 | Galvan-Garza . |

FOREIGN PATENT DOCUMENTS

| | | | |
|---|---|---|---|
| 504234 | 7/1954 | Canada ..................................... | 15/222 |
| 2816963 | 1/1979 | Germany .................................. | 15/222 |
| 14478 | 7/1905 | United Kingdom ..................... | 15/222 |

OTHER PUBLICATIONS

Body Buddy™ website, 6 pp.

Primary Examiner—Randall E. Chin
Attorney, Agent, or Firm—Davis and Bujold

[57] ABSTRACT

A compact applicator (2) for facilitating application of a desired medication, fluid, liquid, lotion, cream, etc. to a desired portion or area of a body of a user. The compact applicator (2) has a pair of opposed handles (12), secured to remote ends (8, 10) thereof which facilitate a rubbing, wiping or application action of the compact applicator (2). A first surface (16) of the compact applicator (2) includes an applicator member (14), e.g. a sponge, which secured thereto by a meshed material. The applicator member (14) receives the desired fluid to be applied and the handles (12) facilitate a wiping or rubbing action of the compact applicator (2) on a desired part of the body, especially the back. The second surface (22) of the applicator member (14) is formed from an absorbent material to facilitate wiping off any excess applied fluid or removing the remaining applied fluid following use. The compact applicator (2) is also provided with an internal compartment (40) which facilitates inversion of the compact applicator (2) into a self-carrying compartment which, when so inverted, has a exposed internal pocket (44) which faces outwardly and can be utilized to carry a desired container.

18 Claims, 6 Drawing Sheets

COMPACT APPLICATOR/REMOVAL SYSTEM

The present invention relates to a flexible, easily transportable and tidy compact applicator, for applying a desired medication, liquid, lotion, cream, substance or some other fluid to a desired surface or area of the human body and, in particular, for allowing a user to apply such fluid to the hard to reach areas of the body such as the back without the aid of another person, as well as facilitating removal of any excess applied medication, liquid, lotion, cream, substance or some other fluid from such hard to reach regions of the body.

BACKGROUND OF THE INVENTION

In the prior art, a variety of different applicators are known for facilitating application of a desired medication, liquid, lotion, cream, substance or some other fluid to a desired portion or area of a body of a user. However, all the known prior art designs are somewhat cumbersome to utilize and are not designed to facilitate ease of self-application of the desired medication, liquid, lotion, cream, substance or some other fluid to areas of the body where it is awkward for a person to apply such fluid without aid and nearly impossible to ensure that proper skin coverage, dosage and/or an appropriate amount has been applied. Nor do these devices facilitate ease of removal of any excess medication, liquid, lotion, cream, substance or some other fluid following application of the same.

Devices for use in reaching a person's back to facilitate bathing are also known in the art. For example, U.S. Pat. No. 5,850,662 to Galvan-Garza discloses a scubber for bathing and scrubbing the back which utilizes an elastic plastic scrubber having two handles to facilitate use behind the back. The Galvan-Garza scrubber is made of a non-absorbent material and does not relate to the presently claimed applicator functions with respect to fluid application and removal nor the compact storage capability of the presently claimed applicator.

SUMMARY OF THE INVENTION

Wherefore, it is an object of the present invention to provide an improved compact applicator for applying a desired medication, fluid, liquid, lotion, cream, etc. which overcomes all the above noted problems associated with the prior art designs.

A further object of the present invention is to provide a compact applicator which is easy to utilize, inexpensive to manufacture and facilitates application of the medication, liquid, lotion, cream, substance or some other fluid to a desired location or body part of a of a user.

Another object of the invention is to provide a removal system, which is integral with the applicator, to facilitate removal of any excess fluid applied to the body as well as to provide a towel for removing excess or unwanted fluid from the hand of a user.

A still further object of the invention is to provide the compact applicator with an internal pouch which allows for convenient and tidy storage as well as transport of the compact applicator.

Yet another object of the invention is to provide a compact applicator which can be washed in a conventional washing machine thereby facilitating ease of maintenance of the compact applicator.

The present invention also relates to a compact applicator for applying a desired fluid, said compact applicator comprising an elongate fabric having opposed first and second surfaces and opposed first and second ends, a pair of handles, one of said pair of handles being secured adjacent the first end of the elongate fabric and the second of the pair of handles being secured adjacent the second end of the elongate fabric and an applicator being secured to the first surface of the elongate fabric, intermediate of the two handles, to facilitate receiving and application of a desired fluid via use of the compact applicator.

The present invention also relates to a method of applying a desired fluid to a human with a compact applicator, the method comprising the steps of providing an elongate fabric with opposed first and second surfaces and opposed first and second ends securing a first one of a pair of handles adjacent the first end of the elongate fabric and securing a second one of the pair of handle adjacent the second end of the elongate fabric and securing a applicator member to the first surface of the elongate fabric, intermediate of the two handles, to facilitate receiving and application of a desired fluid via use of the compact applicator.

DETAILED DESCRIPTION OF THE DRAWINGS

The invention will now be described, by way of example, with reference to the accompanying drawings in which.

DETAILED DESCRIPTION OF THE INVENTION

Figure 1:
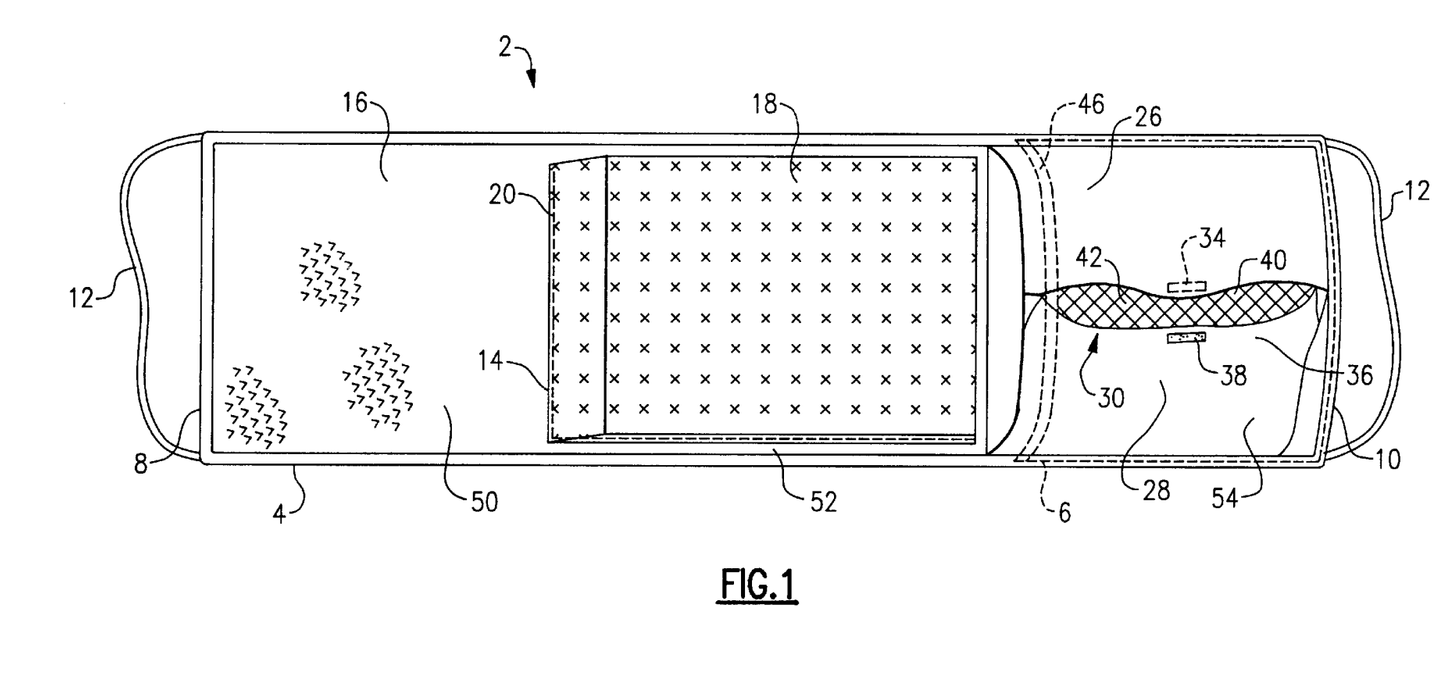
FIG. 1 is a diagrammatic view showing a top surface of the compact applicator according to the present invention.
Figure 2:
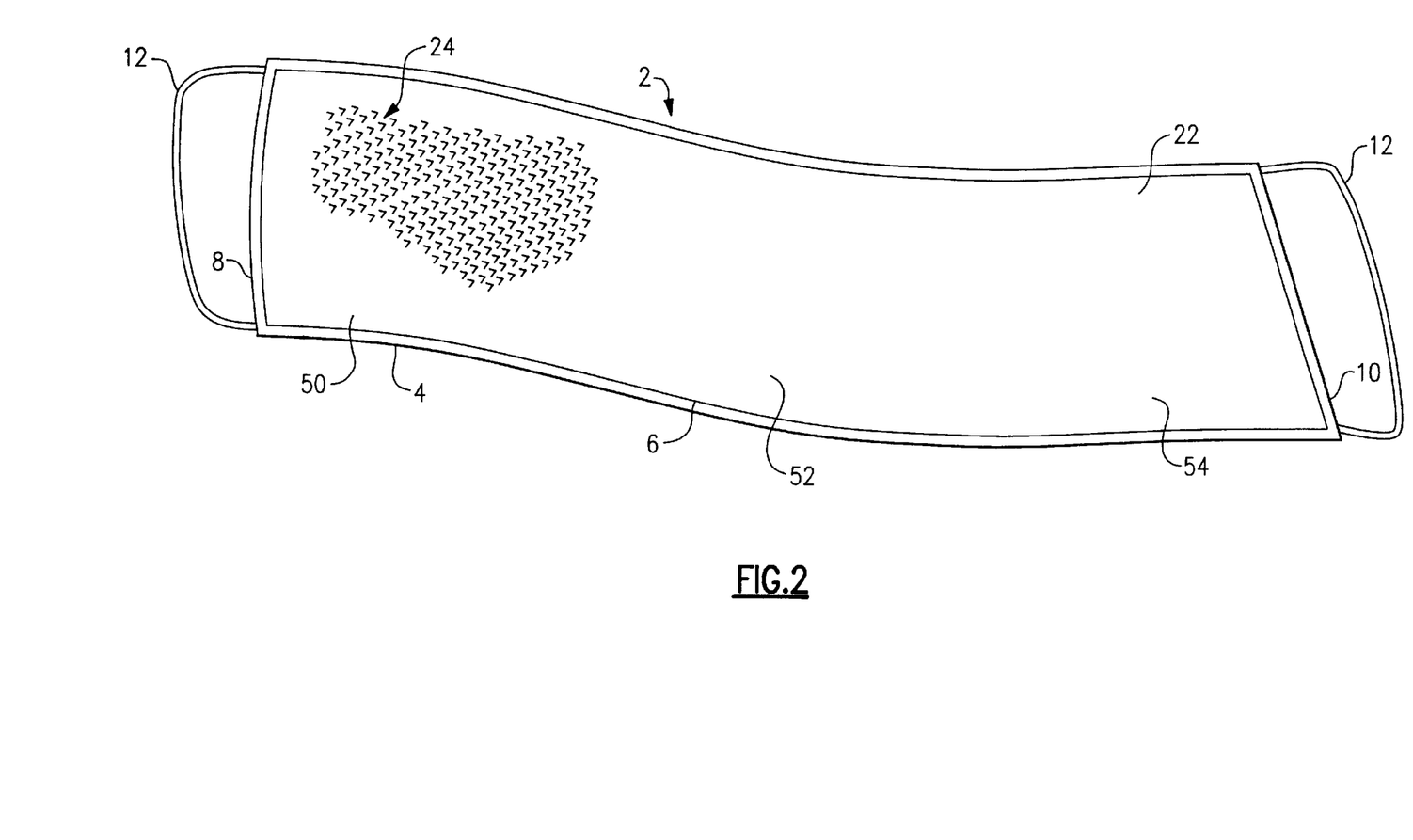
FIG. 2 is a diagrammatic view showing a bottom surface of the compact applicator of FIG. 1.
Figure 3:
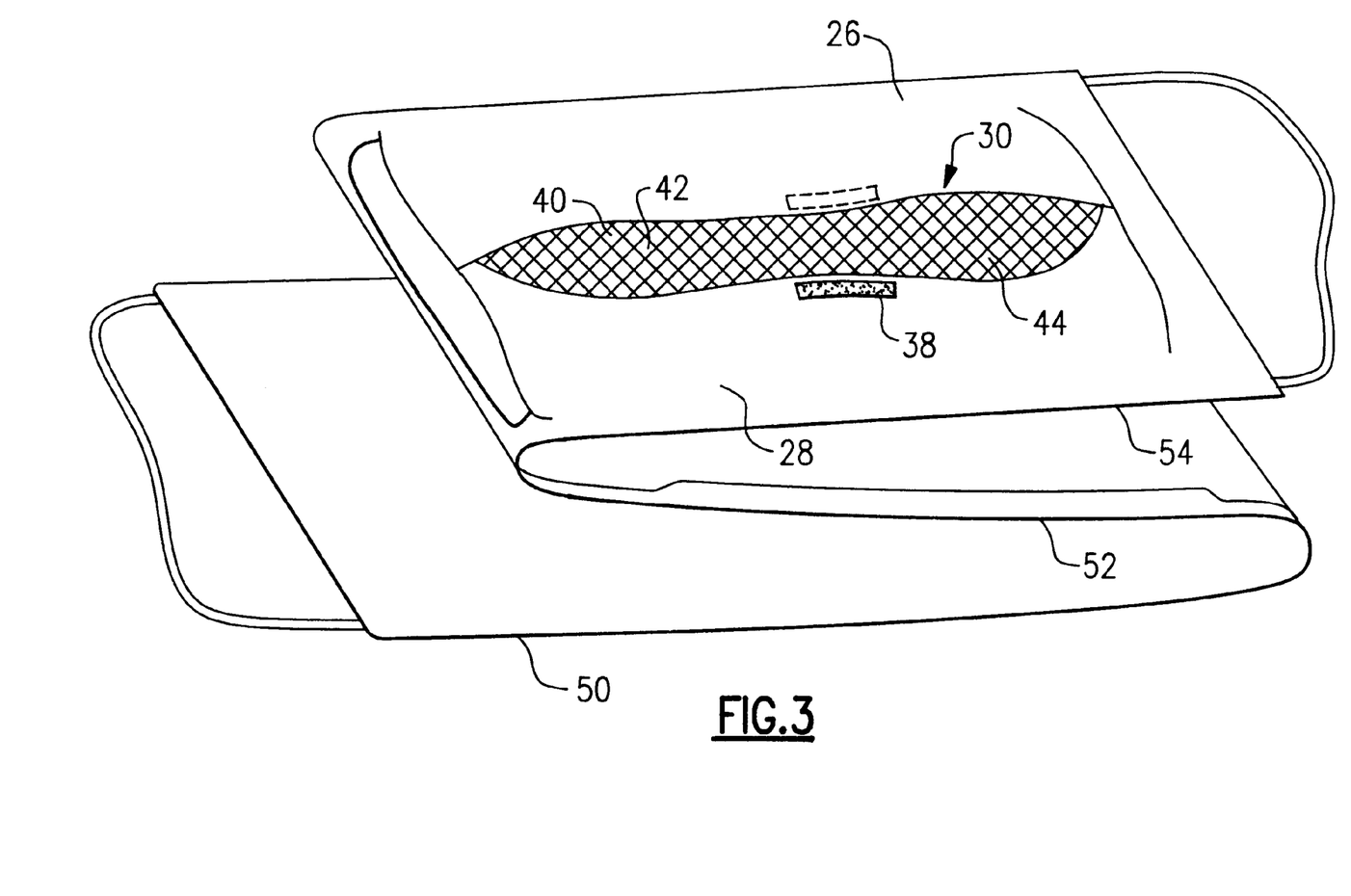
FIG. 3 is a diagrammatic front elevational view of the compact applicator of FIG. 1, shown in a folded state, prior to the internal pocket being inverted.

Turning now to FIGS. 1–3, a detailed description concerning the inventive features of the present invention will now be provided. As can be seen in those Figures, the compact applicator 2, according to the present invention, comprises an elongate strip of a desired, soft flexible fabric 4, e.g. terry cloth or any type of generally absorbent material. The elongate flexible fabric 4 typically has a length of between 12 inches and 36 inches, more preferably a length of between about 18 inches and about 28 inches, and most preferably a length of about 24 inches. In addition, the elongate flexible fabric 4 typically has a width of about 1 inch to 10 inches, more preferably a width of about 2 inches to 6 inches, and most preferably a width of about 3½ inches. As can be seen in FIGS. 1 and 2, the outer periphery of the entire elongate flexible fabric 4 is hemmed or is otherwise bound, indicated as element 6, to prevent unraveling and fraying of the edges of the elongate flexible fabric 4 due to long term continuous use and/or washing. As such binding and hemming is conventional and well known in the art, a further detailed description concerning the same is not provided.

Each remote end 8, 10 of the elongate flexible fabric 4 is provided with a handle 12 to facilitate desired operation of the compact applicator 2. The handles 12, as can be seen in this embodiment, comprise a pair of rope or other type flexible or semi-flexible members which are sewn, stitched, glued, or otherwise attached to or adjacent the remote ends 8, 10 of the elongate flexible fabric 4. The handles 12, if so desired, can be affixed anywhere along the elongate flexible fabric 4, i.e. spaced from the opposed remote ends 8 and 10 anywhere along the elongate flexible fabric 4 or situated directly at each remote end. Further, it is to be appreciated that a variety of different types of handles, which are conventional and well known in the art, can be interchanged with the rope handles shown in the drawings without departing from the spirit and scope of the present invention.

As seen in FIG. 1, an applicator member 14 is supported by an intermediate or central portion of a top first surface 16 of the elongate flexible fabric 4. The applicator member 14 is preferably a sponge or some other absorbent material which facilitates receiving, storing and dispensing a desired quantity of a medication, liquid, lotion, cream, substance or some other fluid to be administered (hereafter referred to as a "fluid") and also facilitates consistent application of the desired fluid to a desired portion or area of the human body when brought into contact therewith.

To facilitate retention of the applicator 14 to the first surface 16 of the elongate flexible fabric 4, the applicator 14 is encased or covered by a meshed material 18 having adequate permeability so as not to significantly hinder the effective receiving and dispensing of the fluid by the applicator 14, but having sufficient composition to encompass and retain the applicator 14. The meshed material 18 is sewn, as indicated by element 20, about its entire perimeter to the first surface 16 of the elongate flexible fabric 4 to facilitate permanent retention of the applicator 14 to the elongate flexible fabric 4. It is to be appreciated, however, that a slit or any other opening can be provided in the meshed material 18 to facilitate replacement of the applicator 14 once it becomes sufficiently soiled and/or spent or to facilitate replacement of the applicator 14 with a more or less porous applicator, depending upon the fluid to be applied, is desired. As such a slit or opening feature is conventional and well known in the art, a further detailed description concerning the same is not provided.

As seen in FIG. 2, the entire opposed second surface 22 of the elongate flexible fabric 4 comprises an absorbent material 24 which preferably has a plurality of loop or pile-type threads, strands or other members to facilitate absorption or removal of unwanted or excess fluid from either the hand or any desired part of the body of a user following application of the desired fluid.

A portion of the first surface 16, located between the applicator 14 and the first remote end 10 of the elongate flexible fabric 4, is provided with a pair of partially overlapping flaps 26, 28 which, when separated from one another, form an opening 30 therebetween. An inwardly facing surface 32 of the overlapped portion of the first flap 26 carries a strip of a male touch fastener 34 while an outwardly facing surface 36 of the overlapped portion of the second flap 28 carries a strip of a mating female touch fastener 38. When the mating male and female touch fasteners 34, 38 are brought into engagement with one another, they securely fasten the two overlapped flaps 26, 28 to one another. The overlapped two flaps 26, 28, together with an outwardly facing surface of the first surface 16 of the elongate flexible fabric 4 serve to define an internal compartment 40.

In addition, a second mesh material 42 is located within the internal compartment 40, and a perimeter portion of the mesh material is located and stitched to both the first and second flaps 26, 28 and the elongate flexible fabric 4, along the interface therebetween, to form an internal pocket 44. A further detailed description concerning the use and/or function of the flaps and the internal compartment and the internal pocket will be provided below.

As can be seen in FIGS. 1 and 2, the compact applicator comprises three segments 50, 52, 54 and the three segments 50, 52, 54 can be folded, into an overlapped accordion-type configuration, as shown in FIG. 3, to facilitate storage of the compact applicator in a compact and tidy manner. It is to be appreciated that the compact applicator can comprise any number of segments depending upon the length of the overall compact applicator 2. When storage of the compact applicator 2 is desired, the compact applicator 2 is typically laid on a table or some other supporting surface with the second surface 22 of the elongate flexible fabric 4 facing and being supported by the supporting surface. With the second surface 22 of the elongate flexible fabric 4 facing the supporting surface, the flaps 26, 28 and internal pocket 44 are inherently facing away from the supporting surface. Thereafter, the second segment 52 of the compact applicator 2 is folded over the first segment 50 and while the third segment 54 is folded over the second segment 52 to result in the configuration generally shown in FIG. 3.

It is to be appreciated that the way the three segments 50, 52, 54, or any other desired number of segments, are folded with one another can vary as long as the first and second flaps 26, 28 and the internal pocket are facing outwardly away from the folded segments. In other words, the segments 50, 52, 54 of the compact applicator 2 should be folded against a rear surface of the compact applicator 2 supporting the first and second flaps, 26, 28 and the internal pocket 44. Such an arrangement is necessary in order to accomplish the desired compact and tidy storage of the applicator as described below and facilitates accommodating the entire compact applicator 2 within the internal compartment 40.

Once the compact applicator 2 is folded into the configuration shown in FIG. 3, the user picks up the compact applicator 2 and grasps the first flap 26 with the fingers of one hand, e.g. his or her left hand, and the second flap 28 with the fingers other hand, e.g. his or her right hand, and pulls the two flaps 26, 28 outwardly away from one another to increase the size of the compartment opening 30. At the same time, the user applies pressure to an outwardly facing central area of the first segment 50 through the judicious use of the opposing thumbs of both hands and biases that central area and perimeter areas of the first segment 50 towards and through the compartment opening formed between the first and second flaps 26, 28. The fingers of both hands then continue to separate the flaps 26, 28 and in conjunction with the opposing thumbs pressing the central and perimeter areas in a direction toward the opening between the pair of flaps 26, 28 until the pair of flaps 26, 28 fully invert thereby at least partially enveloping the folded portion and central areas of the compact applicator 2 within the inverted internal compartment 40.

Figure 4:
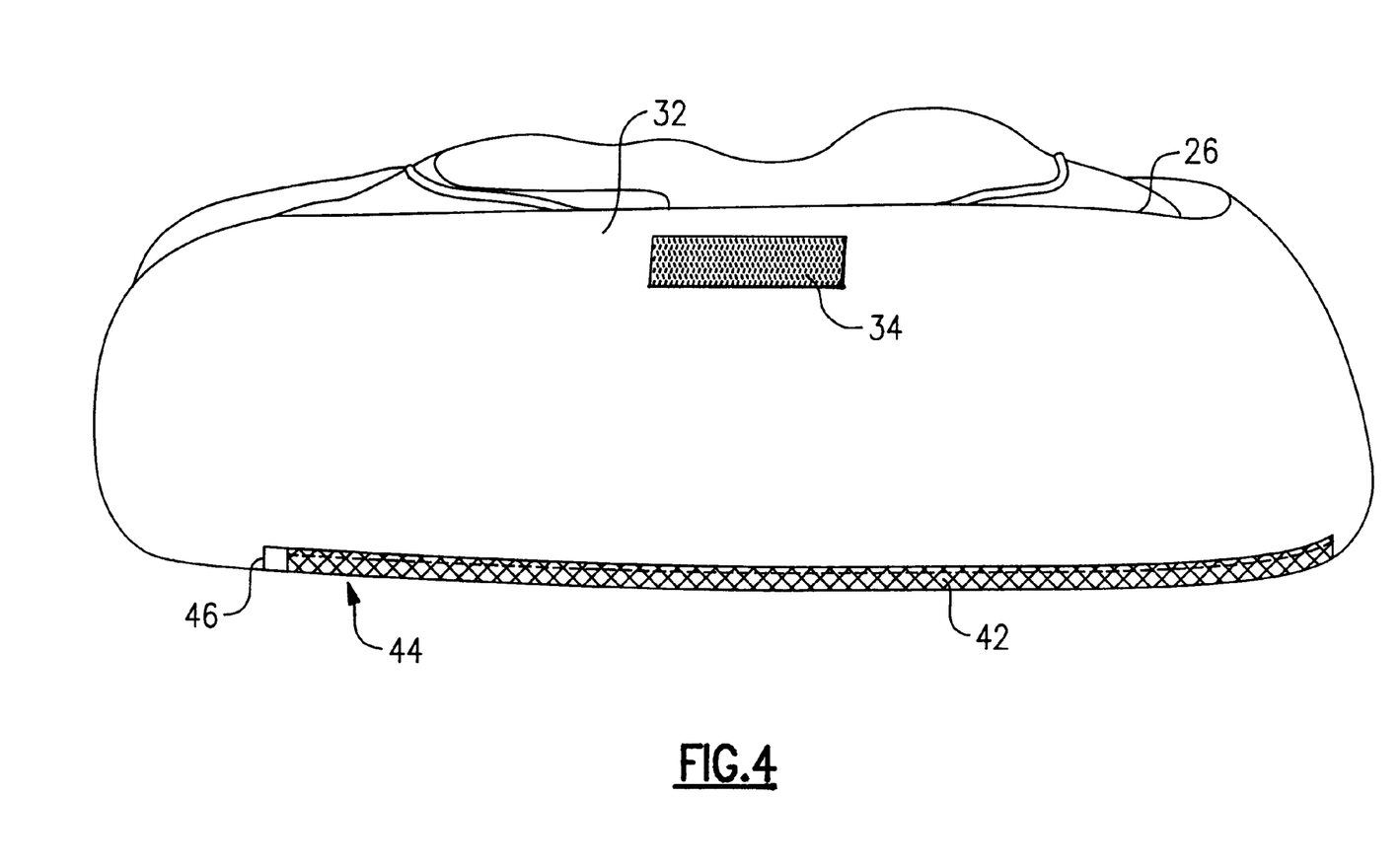
FIG. 4 is a diagrammatic side elevational view of the compact applicator of FIG. 3, following inversion of the internal pouch.

Follow the above inversion process, the compact applicator is now fully inverted and for all essential purposes the pair of flaps 26, 28 and internal pocket 44 are inside out as shown in FIG. 4. The user then continues to "tuck" and/or "work" the three segments 50, 52, 54 into the inverted internal compartment 40 and also "work" the first and second flaps 26, 28 until they completely enclose the folded segments 50, 52, 54 and handles 12 of the compact applicator 2 and the pair of flaps 26, 28 are located adjacent one another.

Figure 5:
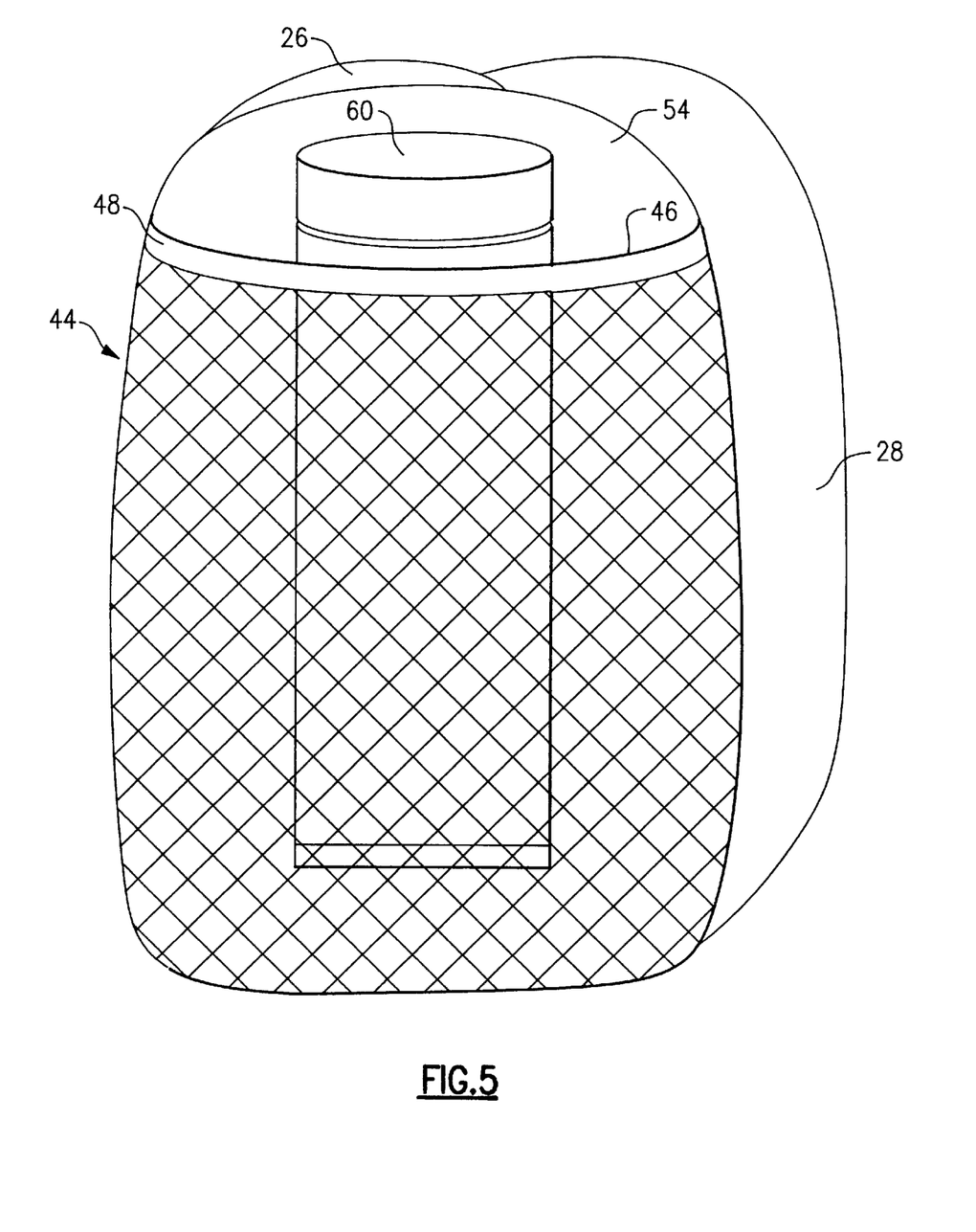
FIG. 5 is a diagrammatic top view showing the inverted internal pouch of FIG. 4 for use in carrying a desired fluid to be applied.
Figure 6:
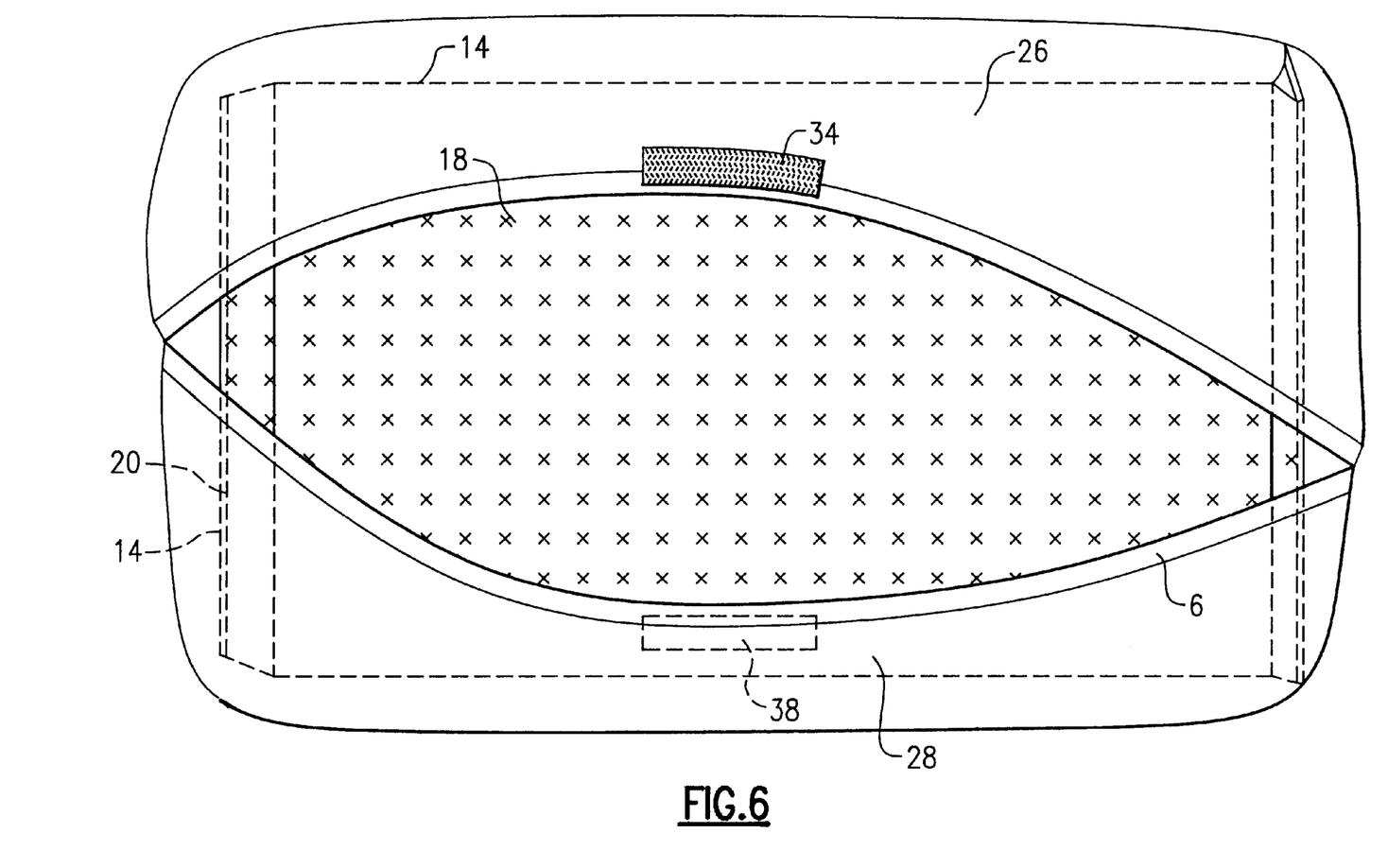
FIG. 6 is a diagrammatic bottom view showing the inverted internal pouch of FIG. 4 for use in carrying a desired fluid to be applied.

Once the compact applicator 2 has been completely accommodated and received within the inverted internal compartment 40 with the flaps 26, 28 again located adjacent one another, the mating male and female touch fasteners 34, 38 can be re-engaged with one another to retain the compact applicator 2 in the inverted state of FIG. 5. It is to be appreciated, as can be seen in FIGS. 5 and 6, for example, once the internal compartment 40 is inverted, the internal mesh pocket 44 is now facing outwardly and thus can be used to retain a desired bottle, container or packet, e.g. suntan lotion, bathing oil, medication, relaxant, etc. In order to facilitate this, the internal pocket 44 is only sewn to both the first surface 16 and the pair of flaps 26, 28 along three perimeter sides while the fourth perimeter side 46 is left un-sewn so as to facilitate placing the container in and withdrawing the container from the internal pocket 44. The fourth unsewn perimeter side 46 may include an elastic band 48 or other type of retaining collar in order to more securely encase the container 60, when contained within the internal pocket 44, while allowing uncomplicated storage and retrieval of the container 60. The fourth un-sewn side 46 could also incorporate a more secure closure, such as a pair of touch fasteners, a mating button(s) and button hole(s), zipper, etc., in order to ensure more complete retention of the container 60.

It is to be appreciated that the shape, size and/or orientation of the above mentioned male and female touch fasteners can vary from application to application. Further, replacement of the male and female touch fasteners 34, 38 with a pair of mating snaps, a button(s) and buttonhole(s), as well as other conventional fasteners could be utilized without departing from the spirit and scope of the present invention.

In the stored or stowed configuration as set forth above (FIGS. 4–6), the sponge 14 and all the surfaces of the applicator 2 that came into contact with the applied fluid during either application or removal of excess fluid are contained within the pouch in a protected manner such that none of the fluid remaining on the sponge and first or second surfaces 16, 22 of the applicator 2 will contaminate the storage environment, for instance when the applicator is stored or stowed in a handbag, a closet or a drawer. Any surrounding articles are prevented from receiving any unwanted or excess fluid due to contact with the applicator 2 by such a tidy compact stored configuration.

Subsequent to storage, retrieval and use of the applicator is performed in a manner exactly opposite to that as described in the above mentioned manner of storing the applicator 2. When application of a desired fluid is necessary, the user removes any article stored within the internal pocket 44, for instance, a container 60 containing a desired fluid, and simply disengages the engaged touch fasteners 34, 38 located on the pair of flaps 26, 28 thereby only partially exposing the stored and inverted applicator 2. By grasping the inverted applicator such that the fingers of each hand respectively peels back one of the pair of flaps 26, 28 while the thumbs "work" and/or apply pressure to an outwardly facing central and perimeter areas of the mesh material 42 towards and through the opening formed between the first and second flaps 26, 28 until the applicator is fully re-inverted and unfolded generally to the configuration shown in FIGS. 1 and 2, hence undoing the inversion process necessary to store the compact applicator 2. Thereafter, the sponge 14 is now exposed in order that fluid may be applied to the sponge.

With the sponge 14 and applicator now exposed, the user may take up for example the desired fluid container and applies any amount needed to the sponge 14. Once a desired amount of fluid is disposed on the sponge, the user grasps the handles 12 at the remote ends 8, 10 of the fabric 4 and in the most convenient and comfortable manner, applies the fluid to any desired body portion via operation of the handles 12 in a to and fro motion to apply and/or wipe a desired area of his or her body.

Since certain changes may be made in the above described invention, without departing from the spirit and scope of the invention herein involved, it is intended that all of the subject matter of the above description or shown in the accompanying drawings shall be interpreted merely as examples illustrating the inventive concept herein and shall not be construed as limiting the invention.

What is claimed is:

1. A compact applicator for applying a desired fluid, said compact applicator comprising:

an elongate fabric having opposed first and second surfaces and opposed first and second ends;

a pair of handles, one of said pair of handles being secured adjacent the first end of the elongate fabric and the second of the pair of handles being secured adjacent the second end of the elongate fabric; and an applicator being secured to the first surface of the elongate fabric, intermediate of the two handles, to facilitate receiving and application of a desired fluid during use of the compact applicator, and one of the first and second surfaces of the compact applicator is provided with an internal compartment to facilitate compact storage of the entire compact applicator when not in use.

2. The compact applicator according to claim 1, wherein the applicator is a sponge member secured to the first surface of the compact applicator.

3. The compact applicator according to claim 2, wherein the sponge is secured to the first surface of the compact applicator via a permeable mesh material sewn to the first surface of the elongate fabric to secure the sponge member to the compact applicator.

4. The compact applicator according to claim 1, wherein the internal compartment is defined by a pair of overlapped flaps and the first surface of the compact applicator.

5. The compact applicator according to claim 4, wherein each of the pair of overlapped flaps is provided with a securing device for securing the pair of overlapped flaps in a partially overlapped configuration.

6. The compact applicator according to claim 5, wherein the internal compartment is sized such that when the internal compartment is turned inside out and inverted, the internal compartment is able to accommodate the compact applicator therein.

7. The compact applicator according to claim 5, wherein the first and second surfaces of the fabric material are at least partially absorbent to facilitate removal of any excess or undesired applied fluid.

8. The compact applicator according to claim 5, wherein the elongate fabric is divided into at least a first segment and a second segment, the first segment supports the internal compartment and the second segment supports the sponge member, and all of the segments are receivably accommodated within the internal compartment when the pouch is inverted.

9. The compact applicator according to claim 8, wherein the internal compartment further comprises an internal pocket, and the internal pocket, when the internal compartment is inverted, faces outwardly and is exposed to facilitate carrying a desired container therein.

10. The compact applicator according to claim 9, wherein the internal pocket is un-sewn along one perimeter side to facilitate releasably retaining a desired-container therein.

11. The compact applicator according to claim 10, wherein the internal pocket includes an elastic member.

12. The compact applicator according to claim 1, wherein the compact applicator is manufactured from an absorbent material and has a length of between 12 inches and 36 inches and has a width of about 1 inch to 10 inches.

13. The compact applicator according to claim 1, wherein the pair of handles comprise at least partially flexible members.

14. The compact applicator for application and removal of a desired fluid to the human body, the compact applicator comprising:

a desired length of flexible, absorbent material having a first end and a second end and having opposed first and second surfaces; the first and second ends being provided with handles for manually manipulating the applicator in order to apply the desired substance to any part of the human body; and one of the first and second surfaces of the compact applicator being provided with an internal compartment to facilitate compact storage of the entire compact applicator when not in use.

15. The compact applicator as set forth in claim 14, wherein at least one of the first and second sides supports a second absorbent material, the second absorbent material facilitates at least one of holding, dispensing and accepting a desired fluid.

16. The compact applicator as set forth in claim 15, wherein the absorbent material further comprises at least three foldable panels, one of said three foldable panels supports the internal compartment, and the remaining foldable panels being foldably accommodated within the internal compartment.

17. The compact applicator as set forth in claim 16, wherein the first side of the panel supporting the internal compartment has two sealable flaps defining an opening, the remaining two panels are folded against the second side of the panel supporting the internal compartment, the second side and panels is enveloped within the internal compartment defined by inversion of the flaps via urging of the opening about the second side and remaining folded panels.

18. A method of applying a desired fluid to a human with a compact applicator, the method comprising the steps of:

providing an elongate fabric with opposed first and second surfaces and opposed first and second ends;

securing a first one of a pair of handles adjacent the first end of the elongate fabric and securing a second one of the pair of handle adjacent the second end of the elongate fabric;

securing an applicator member to the first surface of the elongate fabric, intermediate of the two handles, to facilitate receiving and application of a desired fluid via use of the compact applicator;

using a sponge member as the applicator member and securing the sponge member to the first surface of the compact applicator via a permeable mesh material sewn to the first surface of the elongate fabric;

providing one of the first and second surfaces of the compact applicator with an internal compartment, defined by a pair of overlapped flaps and the first surface of the compact applicator, to facilitate compact storage of the compact applicator when not in use; and providing each of the pair of overlapped flaps with a securing device for securing the pair of overlapped flaps in an overlapped configuration.

* * * * *